United States Patent
Tybinkowski et al.

(10) Patent No.: US 6,519,312 B1
(45) Date of Patent: Feb. 11, 2003

(54) SYSTEM AND METHOD FOR MOUNTING X-RAY TUBE IN CT SCANNER

(75) Inventors: Andrew P. Tybinkowski, Boxford, MA (US); Ronald E. Swain, Reading, MA (US); Michael J. Duffy, Methuen, MA (US); Lidia Nemirovsky, Salem, MA (US)

(73) Assignee: Analogic Corporation, Peabody, MA (US)

( * ) Notice: Subject to any disclaimer, the term of this patent is extended or adjusted under 35 U.S.C. 154(b) by 33 days.

(21) Appl. No.: 09/764,635

(22) Filed: Jan. 18, 2001

Related U.S. Application Data

(60) Provisional application No. 60/225,833, filed on Aug. 16, 2000.

(51) Int. Cl.⁷ .................................................. A61B 6/03
(52) U.S. Cl. ............................... 378/4; 378/15; 378/193
(58) Field of Search ................................. 378/4, 11, 14, 378/205, 207, 193, 197, 15

(56) References Cited

U.S. PATENT DOCUMENTS

| | | | | |
|---|---|---|---|---|
| 4,093,860 A | * | 6/1978 | Kelman et al. | 378/17 |
| 5,054,041 A | | 10/1991 | Hampel | 378/4 |
| 5,427,356 A | * | 6/1995 | Krotov et al. | 182/129 |
| 5,469,429 A | * | 11/1995 | Yamazaki et al. | 378/207 |
| 5,550,886 A | | 8/1996 | Dobbs et al. | 378/19 |
| 5,672,010 A | * | 9/1997 | MacNicol et al. | 384/26 |
| 5,745,548 A | | 4/1998 | Dobbs et al. | 378/207 |
| 5,829,885 A | * | 11/1998 | Scheich | 384/45 |
| 6,188,743 B1 | * | 2/2001 | Tybinkowski et al. | 378/4 |
| 6,337,894 B1 | * | 1/2002 | Tybinkowski et al. | 378/15 |

FOREIGN PATENT DOCUMENTS

EP        1182911 A1 *  2/2001   ............ H05G/1/02

* cited by examiner

Primary Examiner—Drew A. Dunn
(74) Attorney, Agent, or Firm—McDermott, Will & Emery (57) ABSTRACT

The present disclosure provides a system for mounting an x-ray tube to a gantry disk of a CT scanner. The system is designed to make lifting and handling a heavy and cumbersome x-ray tube easier for a person removing or replacing the x-ray tube in a CT scanner. The system includes a harness adapted to be secured to the x-ray tube, at least two elongated rods secured to the harness, and two elongated tracks adapted to be secured to the gantry disk such that the tracks extend generally parallel with a z-axis of the CT scanner. Each track includes a channel for slidingly receiving one of the rods. The present disclosure also provides a method of mounting an x-ray tube in a gantry of a CT scanner. The method includes securing a harness to the x-ray tube, securing elongated rods to the harness such that the rods extend parallel to an axis of the x-ray tube, attaching elongated guides to ends of the rods, inserting distal ends of the guides into channels of elongated tracks in the gantry of the x-ray scanner, and sliding the guides and the rods into the channels of the tracks. Then the guides are removed from the rods, and stops are secured to ends of the tracks to retain the rods within the channels.

24 Claims, 6 Drawing Sheets

SYSTEM AND METHOD FOR MOUNTING X-RAY TUBE IN CT SCANNER

This application claims the benefit of Provisional Application No. 60/225,833 filed on Aug. 16, 2000.

FIELD OF DISCLOSURE

The present disclosure relates to the field of radiography and, in particular, relates to computer tomography ("CT") scanners. Even more particularly, the present disclosure relates to a system and method for mounting an x-ray tube within a CT scanner.

BACKGROUND OF DISCLOSURE

A typical CT scanner includes a gantry comprising an annular frame for rotatably supporting an annular disk about a rotation, or z-axis of the scanner. The disk includes a central opening large enough to receive a patient upon whom a scan is performed. An x-ray tube is positioned on one side of the disk diametrically across the central opening from an array of x-ray detectors. As the disk rotates, the x-ray tube projects a beam of energy, or x-rays, along a scan plane defined by an x-axis and a y-axis of the scanner, through the patient, to the detector array. By rotating the x-ray source about the z-axis and relative to the patient, radiation is projected through the patient from many different directions. An image of the scanned portion of the patient then is constructed from data provided by the detector array.

The x-ray beam directed toward the detector array emanates from a point in the x-ray tube usually referred to as the focal spot. The accurate generation of imaging data requires that the focal spot of the x-ray tube be suitably aligned with the detector array when installing the tube on the disk of the scanner. Usually the x-ray tube is mounted on the CT scanner and the position of the tube continuously adjusted until the correct positioning of the focal spot is empirically determined. This calibration process usually requires the installer to mount the tube as precisely as possible and then run the machine and measure the output of the detectors to determine if the outputs are optimum, or if adjustments are required.

The process of calibrating the position of the x-ray tube on the CT scanner is time consuming, e.g., two to four hours to complete, and costly. Accordingly, there existed a need for pre-calibrating the focal spot prior to installing the x-ray tube into the CT scanner.

In response, U.S. Pat. No. 5,745,548 to Dobbs et al. disclosed a system and method for pre-calibrating the position of a focal spot of an x-ray tube before installation of the x-ray tube in a CT scanner. The pre-calibration is performed using an interface registration support that receives and supports the x-ray tube on a mount provided in either the pre-calibration system or the scanner. The mount of the pre-calibration system duplicates the mount of the scanner, so that a desired position of the focal spot in the scanner is duplicated in the pre-calibration system. Adjustments in the position of the focal spot with respect to the x, y, and z-axes of the scanner are made through the interface registration support. Once adjustments are made, the x-ray tube and the interface registration support can be installed in the CT scanner without the need for subsequent calibration adjustments.

While Dobbs et al. provides a solution for pre-calibrating an x-ray tube prior to mounting the tube in a CT scanner, there still remains the problem of actually mounting the x-ray tube in a scanner. As is known, CT scanners are relatively large structures (the gantry can be about six feet in diameter for example), and an x-ray tube is relatively heavy and bulky (an x-ray tube can weight two hundred pounds or more, for example). An x-ray tube, therefore, can be awkward for one, or even two service people to handle, lift and mount in a CT scanner.

What is still desired therefore is an improved system and method for mounting an x-ray tube in a CT scanner. Preferably the system and method will make handling, lifting and mounting an x-ray tube in a CT scanner easier and less time consuming. In addition, the system and method will preferably allow for pre-calibrating the x-ray tube prior to mounting the tube in the CT scanner.

SUMMARY OF DISCLOSURE

The present disclosure, accordingly, provides a system for mounting an x-ray tube in a gantry disk of a CT scanner. The system includes a harness adapted to be secured to the x-ray tube, at least two elongated rods secured to the harness, and two elongated tracks adapted to be secured to the gantry disk such that the tracks extend generally parallel with a z-axis of the CT scanner. Each track includes a channel for receiving the rods in a sliding manner.

The system is designed to make lifting and handling the heavy and cumbersome x-ray tube easier for a person removing or replacing the x-ray tube in a CT scanner. According to one aspect, the system further includes elongated guides adapted to connect to ends of the rods and guide the rods into the channels of the tracks. According to another aspect, the rods are adjustable with respect to the tracks in a direction parallel to the z-axis of the scanner, such that the position of a focal spot of the x-ray tube can be adjusted along the z-axis. According to an additional aspect, the rods are adjustable with respect to the x-ray tube in a direction generally parallel to an x-axis of the scanner, such that the position of the focal spot can be adjusted along the x-axis. According to a further aspect, the rods are adjustable with respect to the x-ray tube in a direction generally parallel to a y-axis of the scanner, such that the position of the focal spot can be adjusted along the y-axis.

The present disclosure also provides a method of mounting an x-ray tube in a gantry of a CT scanner. The method includes securing a harness to the x-ray tube, securing elongated rods to the harness such that the rods extend parallel to an axis of the x-ray tube, attaching elongated guides to ends of the rods, inserting distal ends of the guides into channels of elongated tracks in the gantry of the x-ray scanner, and sliding the guides and the rods into the channels of the tracks. Then the guides are removed from the rods, and stops are secured to ends of the tracks to retain the rods within the channels.

According to one aspect, the position of the x-ray tube with respect to an x-axis and a y-axis of the scanner is calibrated before mounting the x-ray tube in the gantry. According to another aspect, the circumferential position of the x-ray tube with respect to the harness is calibrated before mounting the x-ray tube in the gantry. According to an additional aspect, the position of the x-ray tube with respect to a z-axis of the scanner is calibrated after mounting the x-ray tube in the gantry.

The foregoing and other features and advantages of the present disclosure will become more readily apparent from the detailed description of the disclosure, as illustrated in the associated drawings.

DETAILED DESCRIPTION OF DISCLOSURE

Figure 1:
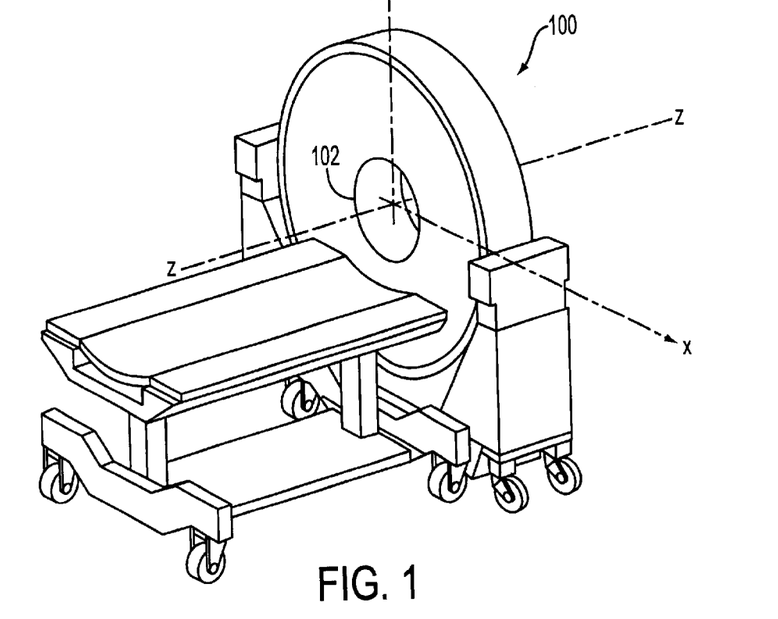
FIG. 1 is a perspective view of an exemplary CT scanner including a mounting system for an x-ray tube constructed in accordance with the present disclosure.
Figure 2:
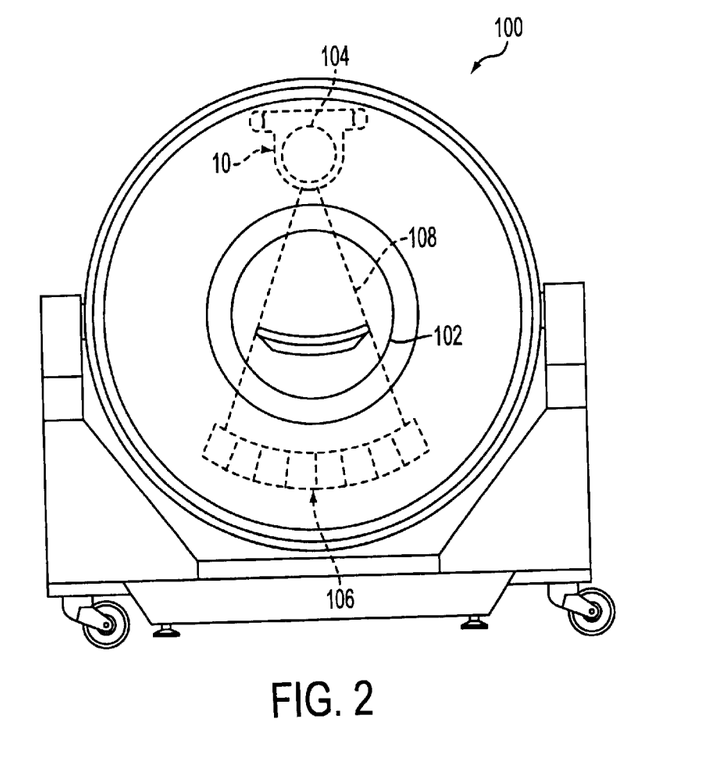
FIG. 2 is a front elevation view of the CT scanner of FIG. 1.

Referring first to FIGS. 1 and 2, in computed tomography, a patient (not shown) to be examined is positioned in a scan circle 102 of a computer tomography (CT) scanner 100, parallel with a z-axis of the scanner, and between an x-ray source, or tube 104 and a rectangular detector array 106. The x-ray tube 104 then projects a beam of energy, or x-rays 108, along a scan plane defined by an x-axis and a y-axis of the scanner 100, through the patient, to the detector array 106. By rotating the x-ray source about the z-axis and relative to the patient, radiation is projected through the patient from many different directions. An image of the scanned portion of the patient then is constructed by a computer from data provided by the detector array 106.

The CT scanner 100 of FIGS. 1 and 2 employs an x-ray tube mounting system 10 constructed in accordance with the present disclosure. The x-ray tube mounting system 10 is shown in greater detail in FIGS. 3 through 5, wherein like reference characters refer to the same parts throughout the different views. Since the mounting system 10, however, secures the x-ray tube to a frame 110 of the CT scanner 100, a description of the frame is presented first.

Figure 3:
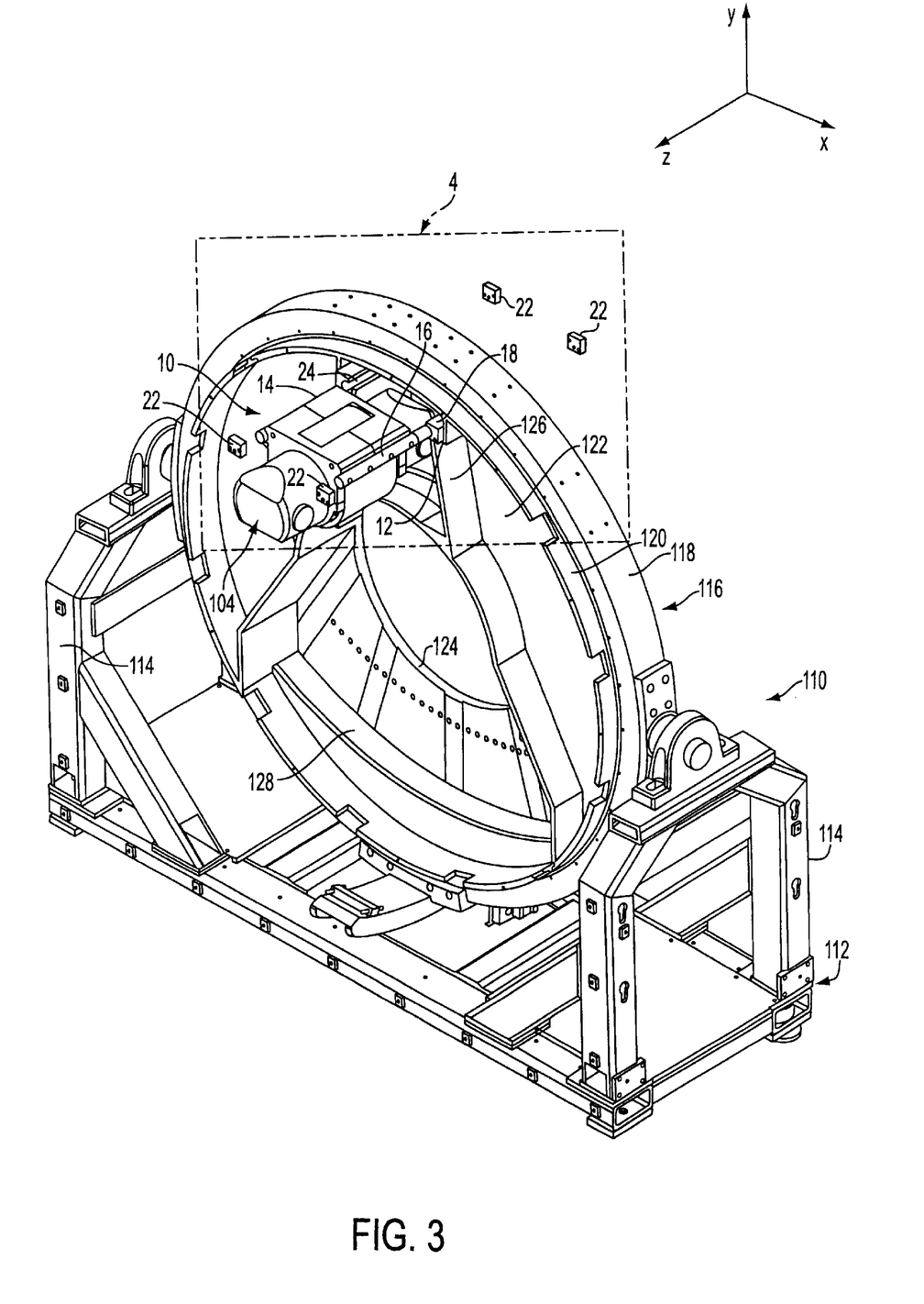
FIG. 3 is a front perspective view of a mounting system constructed in accordance with the present disclosure, and an x-ray tube shown being positioned within a frame of the CT scanner of FIG. 1.
Figure 4:
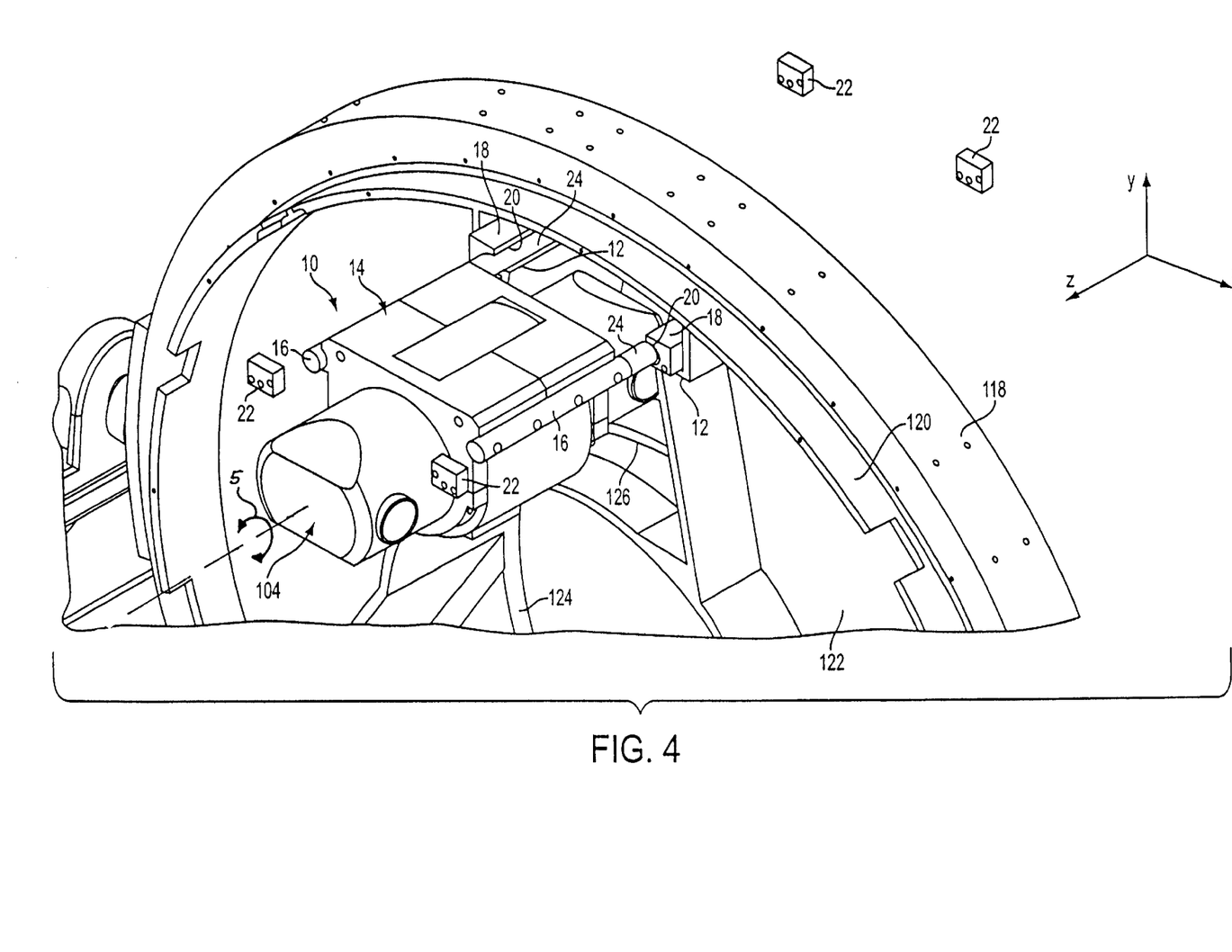
FIG. 4 is an enlarged front perspective view of the mounting system, the x-ray tube and a portion of the CT scanner frame contained in box "4" of FIG. 3.
Figure 6:
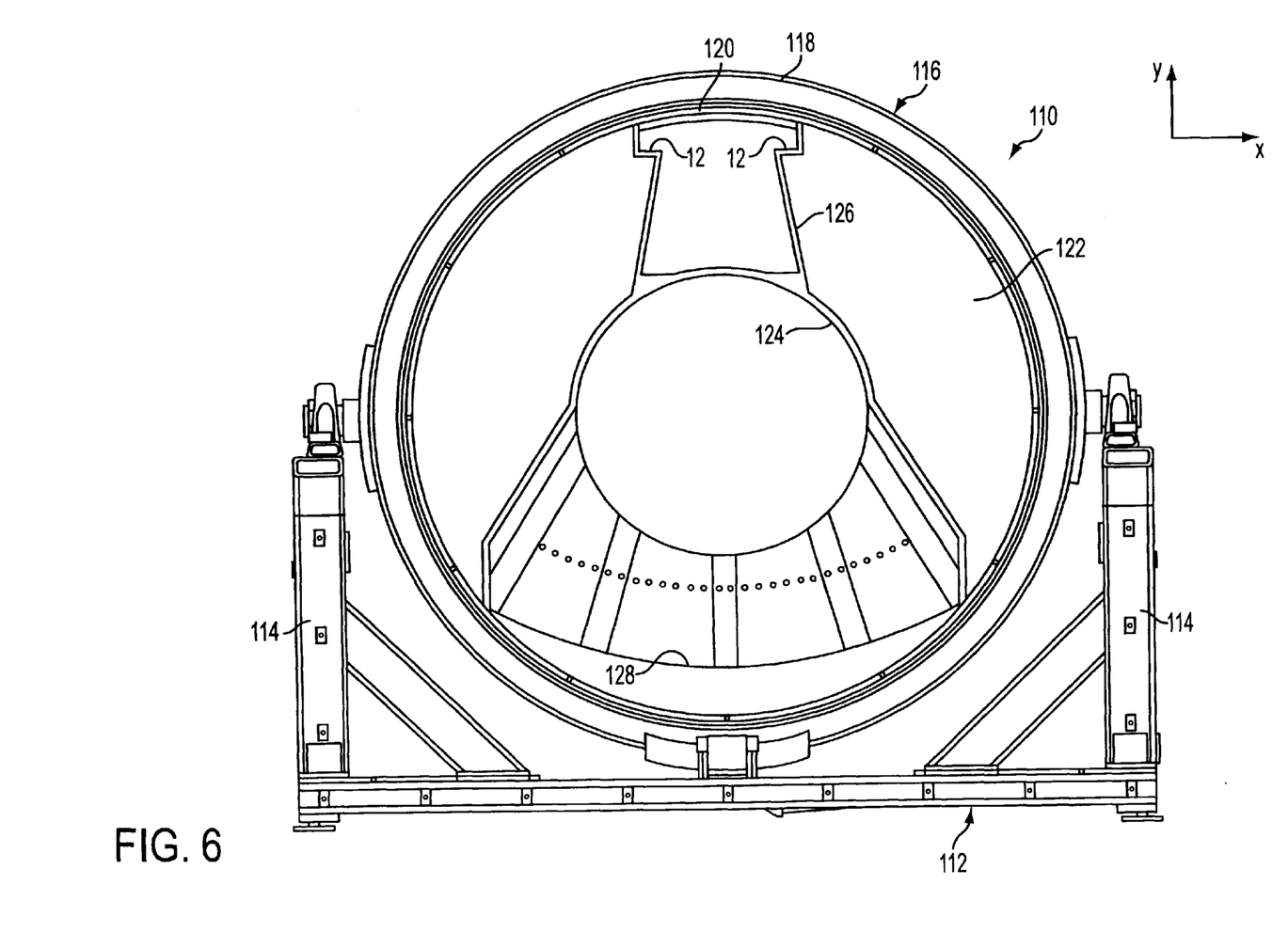
FIG. 6 is a front elevation view of the frame of the CT scanner of FIG. 1, as constructed in accordance with the present disclosure.

FIGS. 3, 4 and 6 show the frame 100 of the CT scanner. The frame 100 includes a stand 112 having two arms 114, and an annular gantry 116 supported between the two arms. The gantry 116 has an outer support 118 pivotally mounted to the arms of the stand, and an inner support 120 that is rotatable within and with respect to the outer support about the z-axis of the scanner. The inner support 120 is adapted to hold x-ray tomography components for rotation therewith during a scanning operation and includes a radially inwardly extending annular disk 122 having a central opening 124. The disk is configured with walls, brackets, bosses and bolt holes for receiving and supporting conventional x-ray tomography components. In particular, the disk 122 includes a first compartment 126 receiving the x-ray tube and a second compartment 128 positioned diametrically opposite the first compartment for receiving the array of x-ray detectors.

As shown best in FIG. 6, the disk 122 includes supports 12 that extend generally parallel with the z-axis of the CT scanner and receive the x-ray tube. Preferably, the supports 12 are provided as a unitary portion of the inner gantry support 120, but can be provided as separate pieces attachable to the disk 122.

Referring back to FIGS. 3 through 5, the mounting system 10 includes a harness 14 adapted to be secured to the x-ray tube 104, at least two elongated rods 16 secured to the harness 14, and two elongated tracks 18 adapted to be secured to the supports 12 of the gantry disk 122 such that the tracks 18 also extend generally parallel with the z-axis of the CT scanner. As shown, each track 18 includes a channel 20 for slidingly receiving one of the rods 16, and stops 22 are provided for being removably secured to ends of the tracks 18 to ensure that the rods 16 remain in the channels 20.

Figure 5:
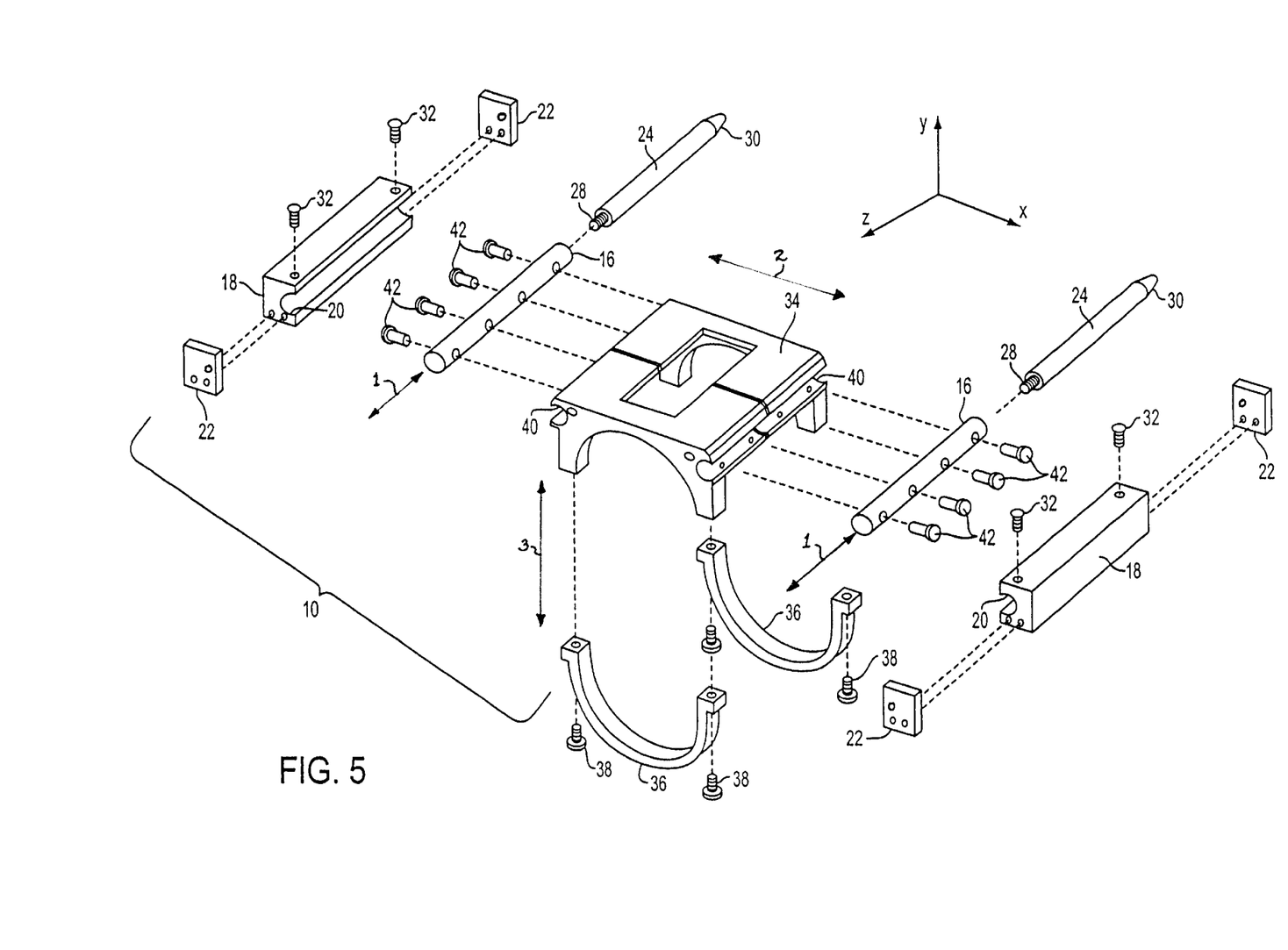
FIGS. 5 and 5A are enlarged and exploded front perspective views of the mounting system of FIGS. 3 and 4.

The system 10 is designed to make lifting and handling the heavy and cumbersome x-ray tube 104 easier for a person removing or replacing the x-ray tube 104 in a CT scanner. It is intended that the rods 16 and harness 14 can be used as handles for easier lifting of the x-ray tube 104.

The mounting system 10 also preferably includes elongated guides 24 adapted to temporarily connect to, and extend coaxially from ends of the rods 16 and guide the rods 16 into the channels 20 of the tracks 18. As shown best in FIG. 5, the guides 24 have threaded fasteners 28 for receipt in threaded bores (not shown) in ends of the rods 16 for removably attaching the guides 24 to the rods 16. Each guide 24 also has a tapered distal end 30 for more easily entering the channels 20 of the tracks 18.

The positions of the rods 16 with respect to the tracks 18 are adjustable in a direction parallel to the z-axis of the scanner, and the tracks 18 include set screws (not shown) which extend through the stops 22 and contact ends of the rods 16 for adjustably securing the rods 16 with respect to the tracks 18, as illustrated by arrows "1" in FIG. 5. Adjusting the rods 16 with respect to the tracks 18, in turn, adjusts the position of the focal spot of the x-ray tube 104 with respect to the z-axis.

The position of the rods 16 with respect to the x-ray tube 104 are also adjustable in a direction generally parallel to the x-axis of the scanner, as illustrated by arrow "2" in FIG. 5. Although not shown, shims are positioned between the rods 16 and the harness 14 for adjusting the rods 16 with respect to the harness 14 in a direction generally parallel to the x-axis of the scanner, as illustrated by arrow "2" in FIG. 5. Adjusting the rods 16 with respect to the harness 14, in turn, adjusts the position of the focal spot of the x-ray tube 104 with respect to the x-axis.

The harness 14 is adjustable with respect to the x-ray tube 104 in a direction generally parallel to the y-axis of the scanner, as illustrated by arrow "3" in FIG. 5. Although not shown, shims are positioned between the harness 14 and the x-ray tube 104 for adjusting the harness 14 with respect to the x-ray tube 104 in a direction generally parallel to the y-axis of the scanner, as illustrated by arrow "3" in FIG. 5. Adjusting the harness 14 with respect to the x-ray tube 104, in turn, adjusts the position of the focal spot of the x-ray tube 104 with respect to the y-axis.

The harness 14 is also adapted to be circumferentially adjustable with respect to the x-ray tube 104. The harness 14 is concentrically received and secured on the x-ray tube 104, and includes a cover 34 and two bands 36 extending from the cover and around the tube 104. Fasteners 38 holding the bands 36 to the cover 34 can be loosened to rotate the x-ray tube 104 with respect to the harness 14 about an axis of the tube 104, as illustrated by arrow "5" in FIG. 4, and thus provide the circumferential adjustment. As shown in FIG. 5, the cover 34 of the harness 14 includes grooves 40 for receiving the rods 16 such that the rods 16 extend parallel with the axis of the x-ray tube 104. The rods 16 are secured in the grooves 40 with suitable fasteners 42.

A method of mounting the x-ray tube 104 in the gantry 116 of the CT scanner generally includes securing the harness 14 to the x-ray tube 104, securing the elongated rods 16 to the harness 14 such that the rods 16 extend parallel to an axis of the x-ray tube 104, and attaching the elongated guides 24 to the ends of the rods 16. The tapered distal ends 30 of the guides 24 are then inserted into the channels 20 of the elongated tracks 18 in the gantry of the x-ray scanner, and the guides 24 and the rods 16 are slid into the channels 20 of the tracks 18 until the rods 16 are between ends of the tracks 18. The guides 24 are then removed from the rods 16, and the stops 22 are secured to the ends of the tracks 18 to retain the rods 16 within the channels 20.

The focal spot of the x-ray tube 104 is calibrated with respect to the x-axis and y-axis of the scanner system prior to the x-ray tube 104 being mounted in the scanner, and adjusted if necessary as described above and illustrated by arrows "2" and "3" in FIG. 5. In addition, the circumferential position of the tube 104 with respect to the harness 14 is also calibrated prior to the x-ray tube 104 being mounted in the scanner, and adjusted if necessary as described above and illustrated by arrow "5" in FIG. 4. A suitable method of pre-calibrating is shown for example in U.S. Pat. No. 5,745,548 to Dobbs et al. entitled "Apparatus for and Method of Adjustably Precalibrating the Position of the Focal Spot of an X-Ray Tube 104 for Use in a CT Scanner", which is assigned to the assignee of the present disclosure and is incorporated herein by reference.

The focal spot of the x-ray tube 104 is calibrated with respect to the z-axis of the CT scanner after the x-ray tube 104 is mounted in the scanner, and adjusted if necessary as described above and illustrated by arrows "1" in FIG. 5. Once the focal spot is determined to be in a preferred position, the set screws (not shown, but which extend through the stops 22) of the tracks 18 are tightened against the ends of the rods 16 to secure the x-ray tube 104 in the preferred position.

Figure 5A:
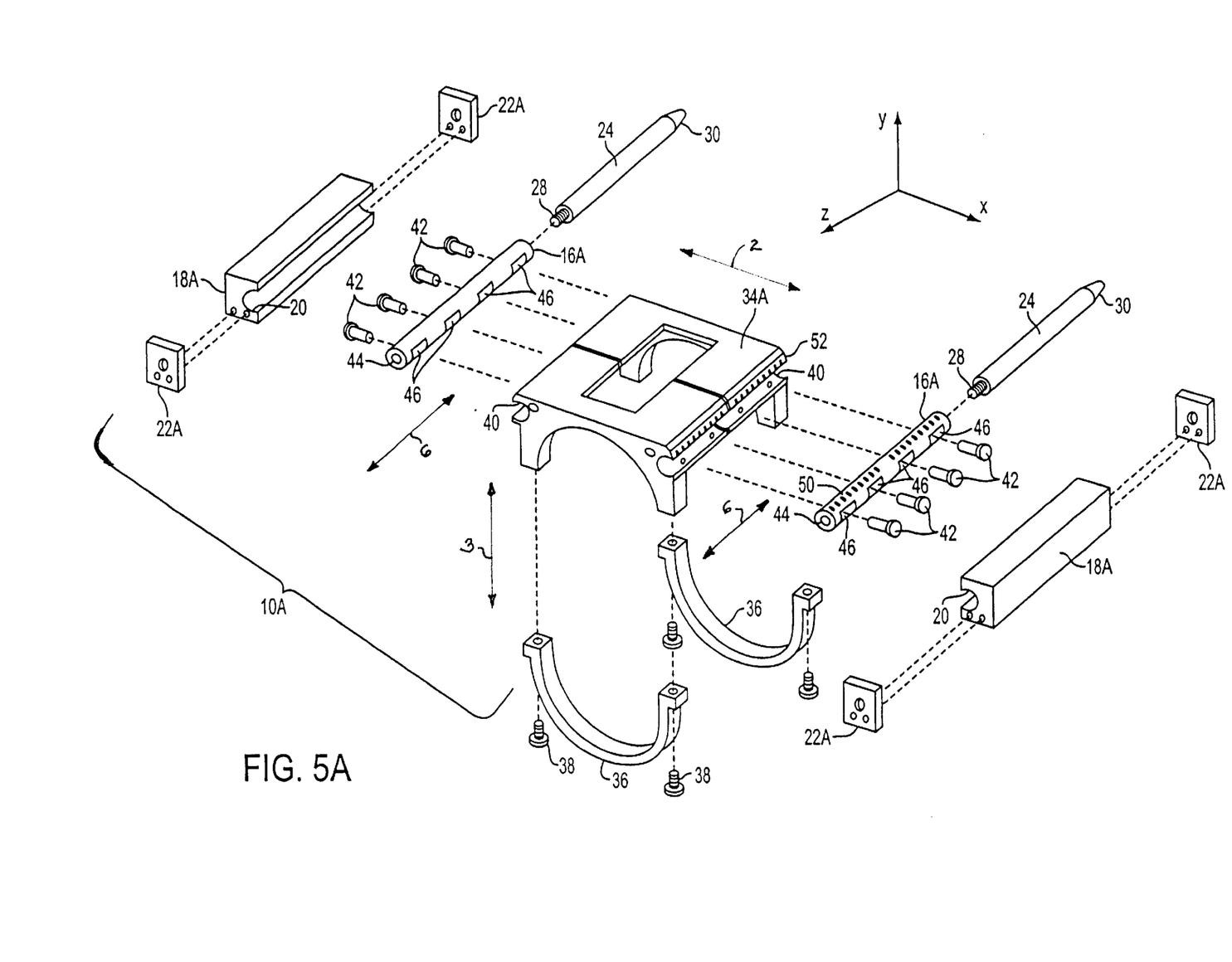

However, another system 10A according to the present disclosure is shown in FIG. 5A which allows for the pre-calibration of the focal spot with respect to the z-axis of the CT scanner. The system 10A of FIG. 5A is similar to the system 10 of FIGS. 3 through 5, and elements that are the same have the same reference numerals.

The system 10A of FIG. 5A includes rods 16A that are substantially the same length as the tracks 18A. In addition, both ends of the rods 16A have fastener openings 44 and stops 22A of the system attach to both the tracks 18A and the rods 16A. Once mounted in the CT scanner, therefore, the positions of the rods 16A with respect to the tracks 18A are fixed and non-adjustable. Instead, the position of the harness 14A with respect to the rods 16A is adjustable, as illustrated by arrow "6", so that the position of the focal spot of the x-ray tube 104 can be calibrated with respect to the z-axis of the CT scanner prior to mounting the x-ray tube 104 in the CT scanner. In particular, the rods 16A have elongated fastener slots 46, which allow for adjustments of the rods 16A with respect to the harness 14A, as illustrated by arrow "6", prior to tightening of fasteners 42. As shown, the rods 16 and the harness 14 may include reference markings 50, 52 to assist in the adjustments.

In sum, the present disclosure provides a system and method for more easily handling, lifting and mounting an x-ray tube in a CT scanner. In addition, the presently disclosed system and method allows the focal spot of the x-ray tube to be pre-calibrated prior to mounting the tube in the CT scanner.

Other modifications and implementations will occur to those skilled in the art without departing from the spirit and the scope of the disclosure as claimed. Accordingly, the above description is not intended to limit the disclosure except as indicated in the following claims.

What is claimed is:

1. A system for mounting an x-ray tube to a gantry disk of a CT scanner, the system comprising:
    an x-ray tube;
    two parallel elongated rods secured to the x-ray tube; and
    two parallel elongated tracks securable to the gantry disk, the tracks including channels for slidingly receiving the rods.

2. A system according to claim 1, further comprising elongated guides adapted to connect to ends of the rods and guide the rods into the channels of the tracks.

3. A system according to claim 1, wherein each guide has a tapered distal end.

4. A system according to claim 1, wherein each rod has a circular cross-section and each channel has a semi-circular cross-section.

5. A system according to claim 1, further comprising stops adapted to be secured to ends of the tracks to contain the rods within the channels.

6. A system according to claim 1, wherein:
    the two parallel elongated tracks are securable to the gantry disk such that the tracks extend parallel with a z-axis of the scanner; and
    the rods are adjustable with respect to one of the x-ray tube and the tracks in a direction parallel to the z-axis of the scanner.

7. A system according to claim 6, wherein the rods are adjustable with respect to the tracks.

8. A system according to claim 7, wherein the tracks include set screws for adjustably securing the rods with respect to the tracks.

9. A system according to claim 1, wherein the rods are adapted to be adjustable with respect to the x-ray tube in a direction generally parallel to an x-axis of the scanner.

10. A system according to claim 9, further comprising shims positioned between the rods and the x-ray tube for adjusting the rods with respect to the x-ray tube in a direction generally parallel to the x-axis of the scanner.

11. A system according to claim 1, wherein the rods are adapted to be adjustable with respect to the x-ray tube in a direction generally parallel to a y-axis of the scanner.

12. A system according to claim 11, further comprising shims for positioning between the rods and the x-ray tube for adjusting the rods with respect to the x-ray tube in a direction generally parallel to the y-axis of the scanner.

13. A system according to claim 1, wherein the x-ray tube is circumferentially adjustable with respect to the rods about an axis of the x-ray tube.

14. A CT scanner frame including a mounting system according to claim 1 and further comprising:
    a stand; and
    an annular gantry mounted on the stand and including an annular disk rotatable about the z-axis of the scanner, the disk having supports supporting the elongated tracks of the x-ray tube mounting system.

15. A CT scanner frame according to claim 14, wherein the supports are unitary with the disk.

16. A method of mounting an x-ray tube in a gantry of a CT scanner, comprising
    securing elongated rods to the x-ray tube such that the rods extend parallel to an axis of the x-ray tube;
    attaching elongated guides to ends of the rods;
    inserting distal ends of the guides into channels of elongated tracks in the gantry of the x-ray scanner;
    sliding the guides and the rods into the channels of the tracks;

removing the guides from the rods; and securing stops to ends of the tracks to retain the rods within the channels.

17. A method according to claim 16, further comprising adjusting the position of the x-ray tube along a z-axis of the scanner after mounting the x-ray tube in the gantry.

18. A method according to claim 16, further comprising adjusting the position of the x-ray tube along a x-axis of the scanner before mounting the x-ray tube in the gantry.

19. A method according to claim 16, further comprising adjusting the position of the x-ray tube along a y-axis of the scanner before mounting the x-ray tube in the gantry.

20. A method according to claim 16, further comprising adjusting the circumferential position of the x-ray tube by rotating the x-ray tube about an axis of the x-ray tube with respect to the rods before securing the rods to the x-ray tube and mounting the x-ray tube in the gantry.

21. A method according to claim 17, wherein the position of the x-ray tube is adjusted along the z-axis of the scanner by adjusting the rods with respect to the tracks in a direction parallel to the z-axis of the scanner.

22. A method according to claim 17, wherein the position of the x-ray tube is adjusted along the z-axis of the scanner by adjusting the rods with respect to the x-ray tube in a direction parallel to the z-axis of the scanner.

23. A method according to claim 18, wherein the position of the x-ray tube is adjusted along the x-axis of the scanner by positioning shims between the rods and the x-ray tube to adjust the position of the rods with respect to the x-ray tube in a direction generally parallel to the x-axis of the scanner.

24. A method according to claim 19, wherein the position of the x-ray tube is adjusted along the y-axis of the scanner by positioning shims between the rods and the x-ray tube to adjust the position of the rods with respect to the x-ray tube in a direction generally parallel to the y-axis of the scanner.

* * * * *